(12) United States Patent
Deevi et al.

(10) Patent No.: US 7,709,264 B2
(45) Date of Patent: May 4, 2010

(54) HANDHELD MICROCANTILEVER-BASED SENSOR FOR DETECTING TOBACCO-SPECIFIC NITROSAMINES

(75) Inventors: Seetharama C. Deevi, Midlothian, VA (US); Fang Tian, Glen Allen, VA (US)

(73) Assignee: Philip Morris USA Inc., Richmond, VA (US)

( * ) Notice: Subject to any disclaimer, the term of this patent is extended or adjusted under 35 U.S.C. 154(b) by 64 days.

(21) Appl. No.: 11/902,041

(22) Filed: Sep. 18, 2007

(65) Prior Publication Data

US 2008/0102532 A1    May 1, 2008

Related U.S. Application Data

(60) Provisional application No. 60/846,090, filed on Sep. 21, 2006.

(51) Int. Cl.
  *G01N 33/00*    (2006.01)
(52) U.S. Cl. .................. 436/107; 422/68.1; 422/88; 73/23.2; 436/518
(58) Field of Classification Search .................. 436/107, 436/518; 422/68.1, 88; 73/23.2
  See application file for complete search history.

(56) References Cited

U.S. PATENT DOCUMENTS

| 5,810,020 | A | 9/1998 | Northway et al. | |
|---|---|---|---|---|
| 6,203,983 | B1 * | 3/2001 | Quate et al. | 435/6 |
| 2003/0209058 | A1 | 11/2003 | Merrill | |
| 2004/0058380 | A1 * | 3/2004 | Levon et al. | 435/7.1 |

(Continued)

FOREIGN PATENT DOCUMENTS

| WO | WO 2005/112670 | * 12/2005 |
|---|---|---|
| WO | WO2005/119233 A | 12/2005 |

OTHER PUBLICATIONS

Fritz, J. et al., "Translating biomolecular recognition into nanomechanics", Science, American Association for the Advancement of Science, US, vol. 288, Apr. 14, 2000, pp. 316-318, XP002365075, ISSN 0036-8075.

(Continued)

*Primary Examiner*—Jill Warden
*Assistant Examiner*—Jonathan M Hurst
(74) *Attorney, Agent, or Firm*—Buchanan Ingersoll & Rooney PC (57) ABSTRACT

A method and system for detecting tobacco-specific nitrosamines. The method includes exposing at least one microcantilever beam to a medium, which may contain tobacco-specific nitrosamines, and measuring a deflection of the microcantilever beam, wherein the deflection indicates a presence of tobacco-specific nitrosamines in the medium. The at least one microcantilever beam can include a silicon base layer and a gold-coated receptor layer with a plurality of thiol molecules having a sulfur head and carboxyl-terminated group. The at least one microcantilever beam can include a silicon base layer and a metal or metal oxide coated receptor layer. Alternatively, the microcantilever beam can be formed by co-absorbing tobacco-specific nitrosamines and silane molecules on a silicon microcantilever surface, wherein the template molecules of tobacco-specific nitrosamines physically co-adsorb between the silane molecules. The template molecules of tobacco-specific nitrosamines are then washed away with a solvent to form a silane monolayer having tobacco-specific nitrosamine cavities.

13 Claims, 7 Drawing Sheets

U.S. PATENT DOCUMENTS

| | | | |
|---|---|---|---|
| 2004/0080319 A1* | 4/2004 | Merrill | 324/439 |
| 2005/0043515 A1 | 2/2005 | Brown et al. | |
| 2005/0199047 A1 | 9/2005 | Adams et al. | |
| 2005/0260423 A1* | 11/2005 | Natesan | 428/447 |
| 2006/0178841 A1 | 8/2006 | Fernandez | |
| 2006/0191320 A1 | 8/2006 | Pinnaduwage et al. | |

OTHER PUBLICATIONS

Moulin, A. M. et al., "Microcantilever-based biosensors", Ultramicroscopy, Amsterdam, NL, vol. 82, No. 1-4, Feb. 2000, pp. 23-31, XP002352331, ISSN 0304-3991.

International Search Report and Written Opinion dated Apr. 10, 2008 for PCT/IB2007/003738.

* cited by examiner

HANDHELD MICROCANTILEVER-BASED SENSOR FOR DETECTING TOBACCO-SPECIFIC NITROSAMINES

CROSS-REFERENCE TO RELATED APPLICATION

This application claims priority to U.S. Patent Provisional Application No. 60/846,090, filed Sep. 21, 2006, which is incorporated herein by this reference in its entirety.

SUMMARY

In accordance with one embodiment, a method of detecting tobacco-specific nitrosamines comprises: at least one microcantilever beam having a molecularly-imprinted monolayer as a receptor layer, wherein the receptor layer can selectively recognize tobacco-specific nitrosamines; exposing the receptor layer coated microcantilever beam to a medium, which may contain tobacco-specific nitrosamines, and measuring a deflection of the microcantilever beam, wherein the deflection indicates a presence of tobacco-specific nitrosamines in the medium.

In accordance with a further embodiment, a method of detecting tobacco-specific nitrosamines comprises: at least one microcantilever beam having a receptor layer of self-assembly monolayer or metal/metal oxide layer, which can selectively recognize tobacco-specific nitrosamines; exposing the receptor layer coated microcantilever beam to a medium, which may contain tobacco-specific nitrosamines, and measuring a deflection of the microcantilever beam, wherein the deflection indicates a presence of tobacco-specific nitrosamines in the medium.

In accordance with another embodiment, a handheld microcantilever-based sensor system adapted to identify tobacco-specific nitrosamines comprises: at least one piezoresistive microcantilever beam having a receptor layer, wherein the receptor layer selectively indicates the presence of tobacco-specific nitrosamines; and a detection system, which outputs an electrical signal upon a resistance change of the at least one microcantilever beam upon exposure to tobacco-specific nitrosamines.

In accordance with a further embodiment, a method of functionalizing a microcantilever beam for detection of tobacco-specific nitrosamines comprises: coating a microcantilever beam with a receptor layer of a molecularly-imprinted monolayer, which can selectively recognize tobacco-specific nitrosamines, wherein exposure of the receptor layer to a medium, which contains tobacco-specific nitrosamines causes a deflection of the microcantilever beam.

In accordance with another embodiment, a method of functionalizing a microcantilever beam for detection of tobacco-specific nitrosamines comprises: coating a microcantilever beam with a receptor layer of self-assembly monolayer or metal/metal oxide layer, which can selectively recognize tobacco-specific nitrosamines, wherein exposure of the receptor layer to a medium, which contains tobacco-specific nitrosamines causes a deflection of the microcantilever beam.

DETAILED DESCRIPTION

Tobacco and tobacco products contain a number of nitrogen-containing substances, which during burning of tobacco, can yield various components in the smoke, such as nitric oxide, nitrogen dioxide, methyl nitrate and tobacco-specific nitrosamines (TSNAs).

Current measurement procedures for sensing and identifying tobacco-specific nitrosamines (TSNAs) are both complicated and costly. Samples such as tobacco are ground, extracted with methylene chloride or alkaline aqueous solutions, and subjected to extensive differential extraction. The final sample is then analyzed by gas chromatography using a thermal energy analyzer for detection (GC-TEA). These currently accepted methods are expensive and time consuming, with a single analyst typically having the capacity to process only 20 samples per eight hour shift. While robotic sample preparation methods exist, the cost is prohibitive.

In addition, tobacco-specific nitrosamine (TSNA) sample preparation generates vast quantities of waste solvent, the disposal of which is also costly. Other currently available instruments to measure tobacco-specific nitrosamines (TSNAs) include gas chromatography (GC), high performance liquid chromatography (HPLC), gas chromatography/mass spectroscopy (GC/MS), thermal energy analyzer (TEA), or combinations thereof. These methods provide accurate identification, quantification, and high detection limits. However, these methods require sophisticated analytical devices and extensive processing of tobacco, which involves considerable amounts of time and power. Therefore, inexpensive tobacco-specific nitrosamines (TSNAs) tests that are fast and easy to perform are in high demand.

Figure 1:
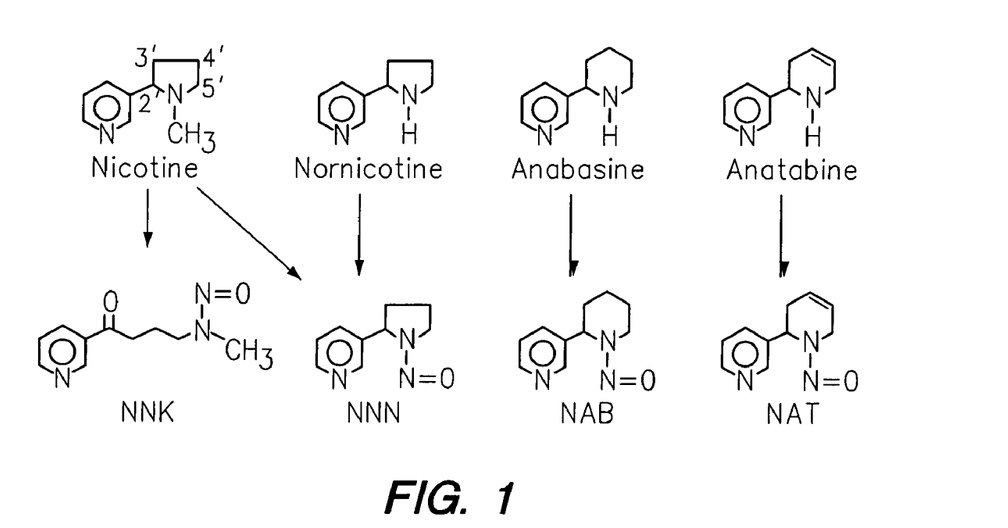
FIG. 1 is the nitrosation of tobacco alkaloids of nicotine, nomicotine, anabasine, and anatabine to form tobacco-specific nitrosamines (TSNAs).

Tobacco-specific nitrosamines (TSNAs) are structurally similar to the nicotine compounds from which they are typically derived. FIG. 1 shows a series of chemical drawings showing the structure of nicotine and several examples of nicotine derivatives including tobacco-specific nitrosamines (TSNAs). As shown in FIG. 1, nitrosamines are chemical compounds of the chemical structure ($R_2$—N—N=O), which are typically produced from nitrites ($NO_2$) and amines ($R_2NH$) under certain conditions, including strong acidic conditions. Tobacco-specific nitrosamines (TSNAs) can be formed during tobacco curing by nitrosation of the tobacco alkaloids. NNN (N'-Nitrosoamine), NAB (N'-Nitrosoanabasine), NAT (N'-Nitrosoanatabine) and NNK (4-(Methylnitrosamino)-1-(3-pyridyl)-1-butanone) are formed predominantly by N-nitrosation of the corresponding secondary amine. NNK can be formed from nicotine by oxidation N-nitrosation following ring openings of the pyrrolidine ring.

In accordance with an embodiment, a sensor based on microcantilever technology can be utilized to offer a reliable handheld device for the detection of trace amounts of tobacco-specific nitrosamines (TSNAs) having a detection range of 400 ppb to 50,000 ppb. In addition, it can be appreciated that microcantilever sensor technology can offer a handheld, real-time sensor for chemicals, either in gaseous or in liquid phase, including high sensitivity, miniature size, low power consumption, and the ability to fabricate into an array for simultaneous detection of a number of chemicals. Accordingly, it would be desirable to have a handheld microcantilever-based sensor system capable of sensing and identifying trace amounts of tobacco-specific nitrosamines (TSNAs).

Microcantilevers are micro-electromechanical systems (MEMs) that can be micromachined and mass-produced from single crystal silicon wafers. Microcantilevers offer high sensitivity and selectivity for a wide variety of biological and chemical sensing. Ions ($Hg^{2+}$, $Cu^{2+}$, $Ca^{2+}$, $CrO_4^{2-}$, etc.) and chemical vapors can be detected with sub-parts per billion sensitivity or better. Biological applications include DNA hybridization and antigen-antibody binding.

According to an embodiment, cantilevers or microcantilevers are microfabricated beams of silicon, which can be functionalized to detect the presence of tobacco-specific nitrosamines using the surface of a microcantilever beam. If the surface of the microcantilever beam is functionalized in such a way that a chemically active and a chemically inactive surface is obtained, chemical or physical processes on the active cantilever surface can be observed using the temporal evolvement of the cantilever's response. Cantilevers can be used as a nanomechanical sensor device for detecting chemical interactions between bonding partners on the cantilever surface and in its environment. At the interface between an active cantilever surface and the surrounding medium, the formation of induced stress, the production of heat or a change in mass can be detected. In general, one of the bonding partners is placed on a cantilever, while the other bonding partners are present in the environment.

In an embodiment, the microcantilever-based sensors can measure the induced surface stresses arising from the surface reconstruction and/or reorganization associated with a molecular adsorption or desorption on the surface of the microcantilever beam. Specificity and sensitivity of microcantilever-based sensors can be achieved by functionalizing one side of the microcantilever surface with a uniform specific receptor layer. The opposite side is typically rendered inert or chemically inactive. For example, in accordance with an embodiment, the opposite side is preferably inert or chemically inactive to a medium containing tobacco-specific nitrosamines (TSNAs). In the case of an array of microcantilever beams, it can be appreciated that the microcantilever beams can coated with different receptor materials. In addition, it can be appreciated that the ability to select and coat a receptor material uniformly on the surface of a base layer of single crystal silicon is preferred for both selectivity and sensitivity.

Figure 2:
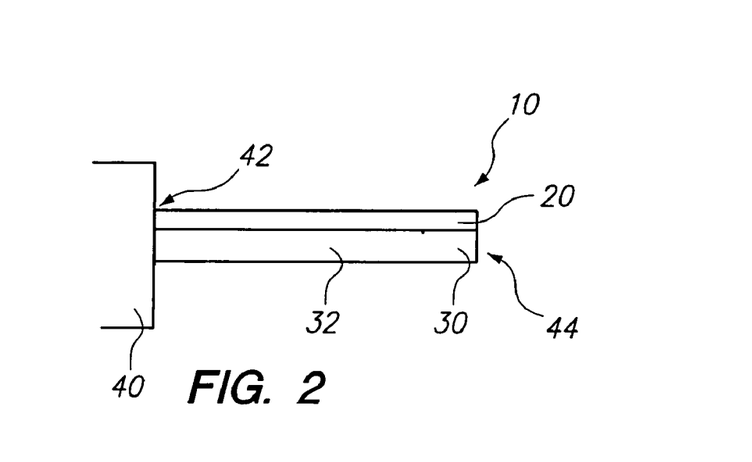
FIG. 2 is a cross sectional view of an unexposed microcantilever beam in accordance with an embodiment.

FIG. 2 shows a cross sectional view of an unexposed microcantilever beam 10 in accordance with an embodiment. The microcantilever beam 10 is comprised of a receptor layer 20 and a base layer 30. The receptor layer 20 is adapted to detect and sense tobacco-specific nitrosamines (TSNAs). The base layer 30 is preferably produced from a single crystal silicon (Si) material or wafer 32. It can be appreciated that the receptor layer 20 can be deposited on the base layer 30. As shown in FIG. 2, the microcantilever beam 10 has a first end 42, which is held at a fixed location 40, and a second end 44, which is free to deflect or bend upward and downward.

Figure 3:
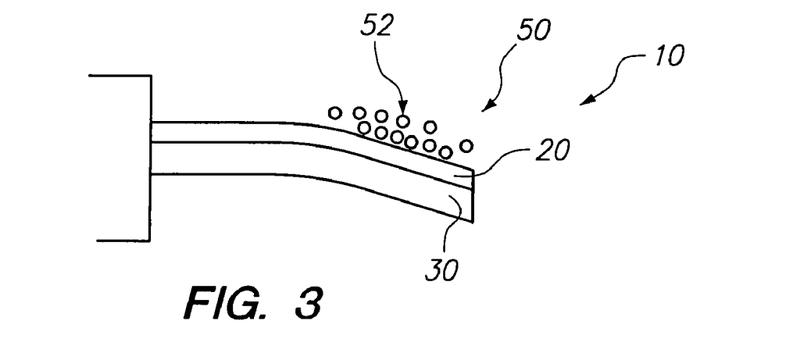
FIG. 3 is a cross sectional view of a microcantilever beam exposed to a medium containing tobacco-specific nitrosamines (TSNAs).

FIG. 3 shows a cross sectional view of the microcantilever beam 10 of FIG. 2, wherein the receptor layer 20 physically and/or chemically reacts with one or more of the molecules 52 in a medium 50. As shown in FIG. 3, the physical or chemical reaction of the one or more molecules 52 within the medium 50 produces a stressed-induced deflection or bending of the cantilever beam 10 at a nano-length scale. The stress-induced deflections may be brought about by volume changes due to the physical and/or chemical interactions of the receptor layer 20 and the one or more molecules 52 (e.g., tobacco-specific nitrosamines (TSNAs)) within the medium 50. The deflection or bending of the microcantilever beam 10 is then preferably measured using an optical, a piezo-electric, or other suitable methods to detect and quantify the presence of the one or more molecules 52 (e.g., tobacco-specific nitrosamines (TSNAs)) within the medium 50.

Figure 4:
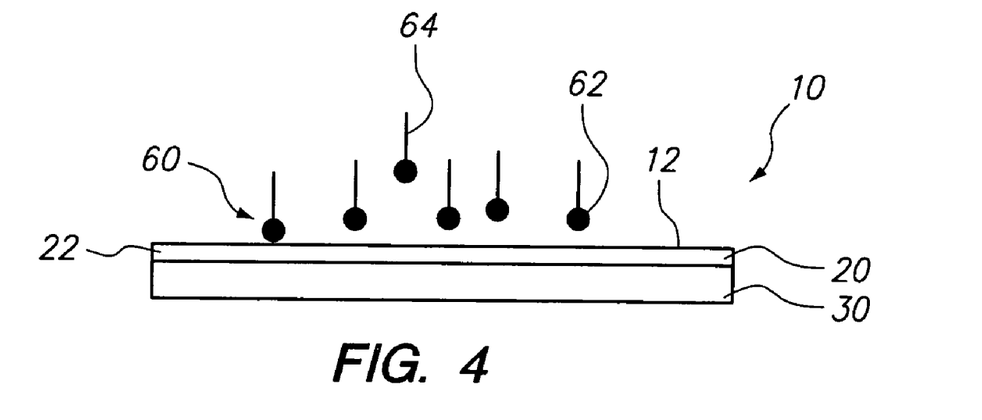
FIG. 4 is a cross sectional view of a thiol-based self-assembly process, which can be used for functionalizing a microcantilever beam.

FIG. 4 shows a cross sectional view of a thiol-based self-assembly process on a surface 12 of a gold-coated microcantilever beam 10. The thiol-based self-assembly process comprises the functionalizing of the gold-coated microcantilever beam 10 with a monolayer of thiol molecules 60. As shown in FIG. 4, the microcantilever beam 10 includes a base layer 30, which is preferably silicon, and a receptor layer 20 comprised of a gold (Au) substrate 22. It can be appreciated that a chromium or titanium adhesion layer (not shown) can be added to the base layer 30 prior to the deposition of the gold layer 22. The surface 12 on the gold substrate 22 is configured to receive a plurality of thiol molecules 60 having a sulfur atom or sulfur head group 62 with a carboxyl-terminated group 64, —COOH, wherein the sulfur atom or sulfur head group 62 undergoes chemisorption with the gold-coated receptor layer 20.

Figure 5:
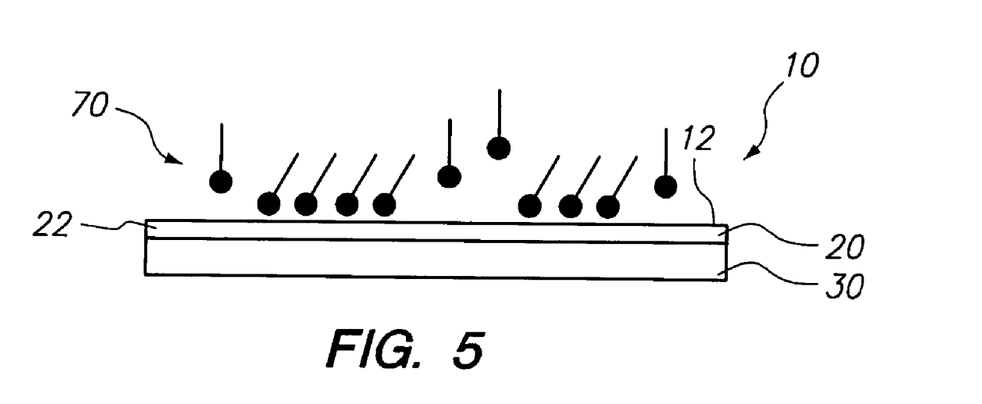
FIG. 5 is a cross sectional view of the thiol-based self-assembly process as shown in FIG. 4.

FIG. 5 shows a cross sectional view of the thiol-based self-assembly process as shown in FIG. 4, wherein the thiol molecules 60 with carboxyl-terminated group 64, —COOH, begins the self-assembly process of forming a monolayer 70 of thiol molecules 60 with a carboxyl-terminated group 64 on the gold-coated receptor layer 20.

Figure 6:
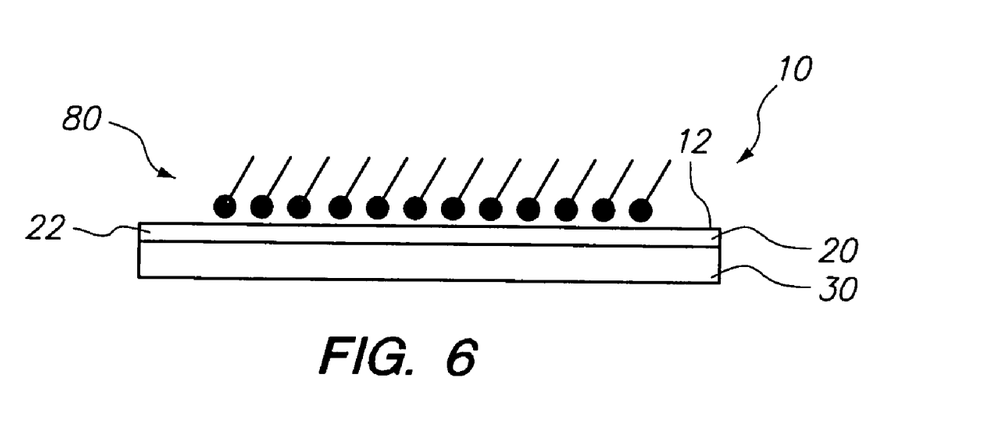
FIG. 6 is another cross sectional view of the thiol-based self-assembly process as shown in FIG. 4.

FIG. 6 shows another cross sectional view of the thiol-based self-assembly process as shown in FIG. 4, wherein the thiol molecules 60 have formed a fully formed a self-assembled monolayer 80 (SAMs) of thiol molecules 60. It can be appreciated that as shown in FIG. 6, the thiol self-assembled monolayer 80 (SAMs) coated microcantilever beam 10 will undergo a bending when exposed to tobacco-specific nitrosamines (TSNAs).

Figure 7:
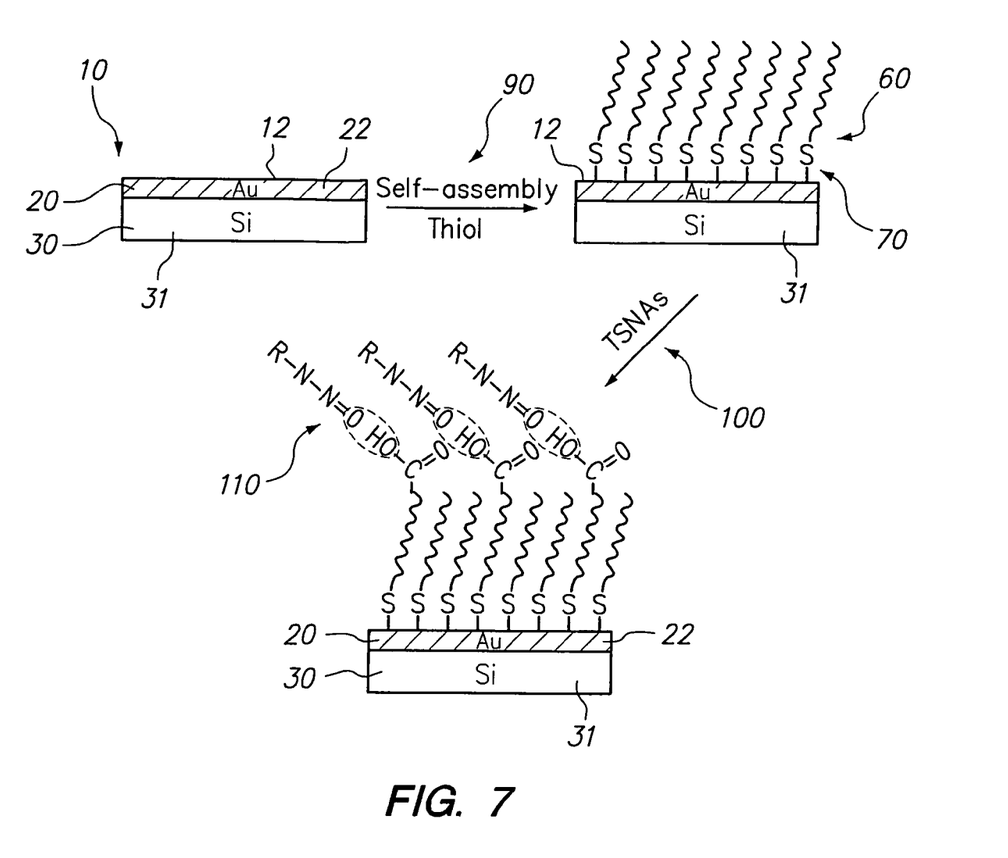
FIG. 7 is a schematic diagram of a further embodiment of a thiol-based self-assembly process, which can be used for functionalizing a microcantilever beam.

FIG. 7 shows a schematic diagram of a method of formation of a thiol-based self-assembly process on a microcantilever beam 10 as show in FIGS. 4-6. As shown in FIG. 7, the thiol-based self-assembly process comprises the functionalizing of a gold (Au) coated microcantilever beam 10 with thiol molecules 60 with carboxyl-terminated groups 64. The microcantilever beam 10 includes a base layer 30 comprised of a silicon substrate 31 and a gold substrate 22. The gold-coated microcantilever beam 10 receives a plurality of thiol molecules 60, wherein the sulfur atom or sulfur head 62 group undergoes chemisorption with the gold substrate 22. In step 90 of the thiol-based self-assembly process, the thiol molecules 60, which includes a carboxyl-terminated group 64, —COOH, begins the self-assembly process of forming a monolayer 70 of thiol molecules 60 with a carboxyl-terminated group 64 on the gold surface of the microcantilever beam 10. Once the thiol molecules 60 have formed a fully formed a self-assembled monolayer 80 (SAMs) of thiol molecules 60, as shown in step 100, the beam 10 will undergo a bending when exposed to tobacco-specific nitrosamines (TSNAs) 110 due to the strong hydrogen bonding between the —COOH group in the self-assembled monolayer (SAMs) and the —N—N═O group, basic pyrrolidine-N and pyridine-N of the tobacco-specific nitrosamines (TSNAs). In accordance with an embodiment, the terminal group in the thiol molecule is comprised of —OH, —$NH_2$ or —COOH moieties. In addition, the hydrocarbon chain of the thiol molecules preferably includes 6 to 22 carbon atoms.

In accordance with a further embodiment, the method of detecting tobacco-specific nitrosamines can include at least one microcantilever beam 10 having a receptor layer 20 comprised of a metal, such as aluminum (Al), platinum (Pt) or palladium (Pd), or a metal oxide layer, which can selectively recognize tobacco-specific nitrosamines (TSNAs). The receptor layer 20 is preferably exposed to a medium, which may contain tobacco-specific nitrosamines, and wherein a deflection of the microcantilever beam 10 indicates a presence of tobacco-specific nitrosamines in the medium.

Figure 8:
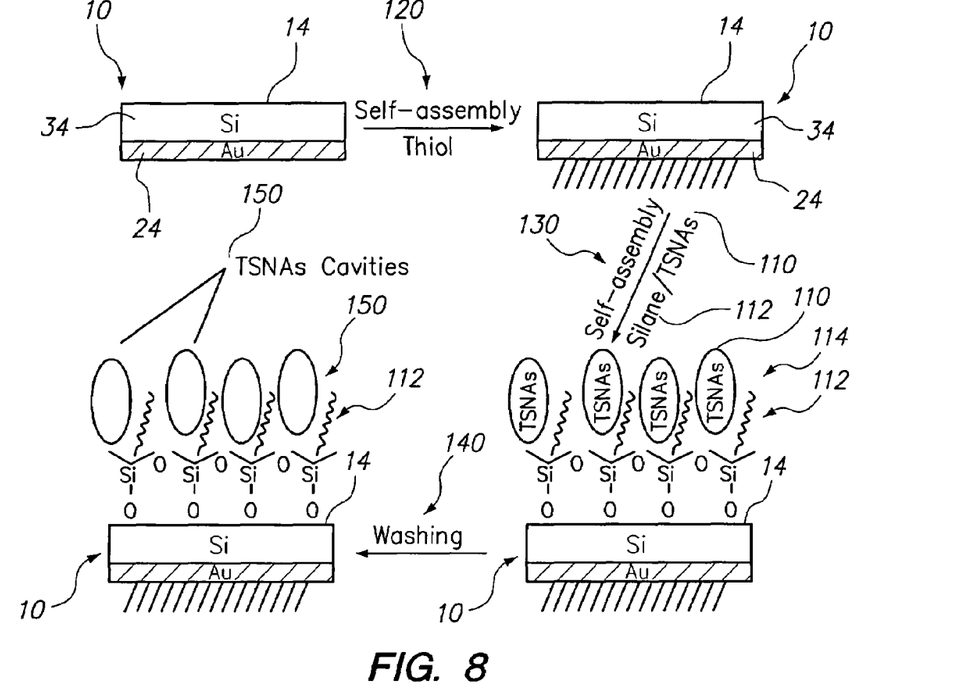
FIG. 8 is a schematic diagram of a method of formation of selective tobacco-specific nitrosamines (TSNAs) cavities on a microcantilever surface using a molecular imprinting technique.

FIG. 8 shows a schematic diagram of a method of formation of selective tobacco-specific nitrosamine (TSNA) cavities 150 on a surface 14 of a silicon microcantilever beam 10 in accordance with one embodiment. As shown in FIG. 8, the microcantilever beam 10 is preferably comprised of a base layer 34 of silicon substrate, and a layer 24 of gold. The layer 24 of gold or gold side of the microcantilever beam 10 is first blocked by self-assembling thiol monolayer as shown in step 120. In accordance with an embodiment, the hydrocarbon chain of the thiol molecules is comprised of 6 to 18 carbon atoms. The selective tobacco-specific nitrosamines (TSNAs) cavities 140 are formed utilizing a silane-based self-assembly and molecular imprinting technique as shown in step 130, wherein tobacco-specific nitrosamines (TSNAs) 110 are co-adsorbed with silane molecules 112 on the silicon microcantilever surface 14. The template molecules 114 of tobacco-specific nitrosamines (TSNAs) 110 co-adsorb between the silane molecules 112. In accordance with an embodiment, the hydrocarbon chain of the silane molecules 112 is comprised of 6 to 18 carbon atoms.

In step 140, the template molecules 114 of tobacco-specific nitrosamines (TSNAs) 110 are then rinsed or washed away with a suitable solvent forming tobacco-specific nitrosamines (TSNAs) cavities 150 on the self-assembly monolayer (SAM). The self-assembled monolayer with the tobacco-specific nitrosamine cavities 150 as shown in FIG. 8 provides a method of detecting tobacco-specific nitrosamines (TSNAs) 110 as a result of the specific physical molecular recognition of the tobacco-specific nitrosamines 110 (TSNAs) within the tobacco-specific nitrosamine cavities 150 on the microcantilever beam 10.

Figure 9:
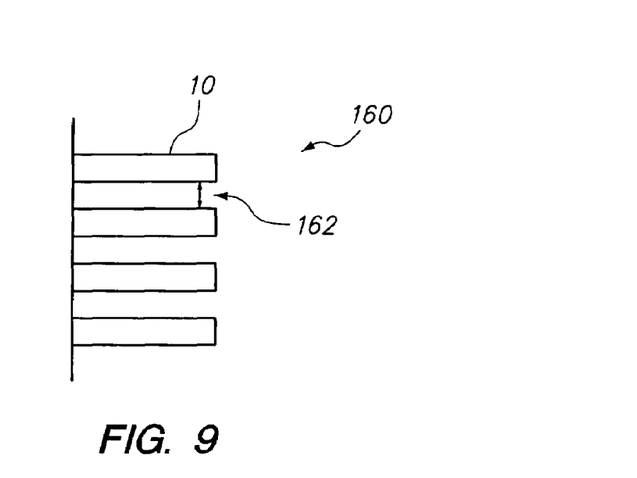
FIG. 9 is an array of microcantilever beams in accordance with an embodiment.

FIG. 9 shows an array 160 of microcantilever beams 10 in accordance with embodiments. As shown in FIG. 9, the array 160 is preferably comprised of at least two (2), and more preferably at least four (4), and most preferably four to sixteen (4-16) microcantilever beams 10. The array 160 of microcantilever beams 10 is preferably independently addressable, wherein each microcantilever beam 10 effects output of a detection signal, independent of the other microcantilever beams 10. It can be appreciated that the array 160 can be one-dimensional (e.g., 1×4) as shown in FIG. 9, two dimensional, (e.g., 2×2), or any other suitable configuration. The microcantilever beams 10 will be separated by a space 162 between 50 to 500 micrometers wide and more preferably the space 162 is between 100 to 300 micrometers apart. In addition, the microcantilever beams 10 preferably have an overall length of 100-400 μm, a width of 20-70 μm, and a thickness of 0.5-1.5 μm, and more preferably an overall length of about 120-150 μm, a width of about 25-50 μm, and a thickness of about 0.75-1.25 μm. In addition, each microcantilever beam 10 preferably has a spring constant of between about 0.4 to 0.8 N/m.

The array 160 of microcantilever beams 10 will preferably be fabricated into a single chip, wherein the small dimensions of the array 160, which may render the array 160 of microcantilever beams 10 sensitive to many different parameters, such as temperature and mechanical vibrations. Therefore, it can be appreciated that any device incorporating an array 160 of microcantilever beams 10 will preferably include electronic components or devices to suppress the background noise, and monitor and evaluate the electronic output from each of the microcantilever beams 10. It can be appreciated that any suitable fabrication technique, which can precisely functionalize each individual microcantilever beam 10 with a receptor layer, can be used. In addition, as set forth above, the microcantilever beams 10 are preferably integrated into a single chip, wherein a sample cell with a flow and volume controlled system to introduce a medium 50 having tobacco-specific nitrosamines (TSNAs) 110 so as to expose the medium 50 to the microcantilever beam 10 (e.g., the medium 50 can be a gas or a liquid).

Figure 10:
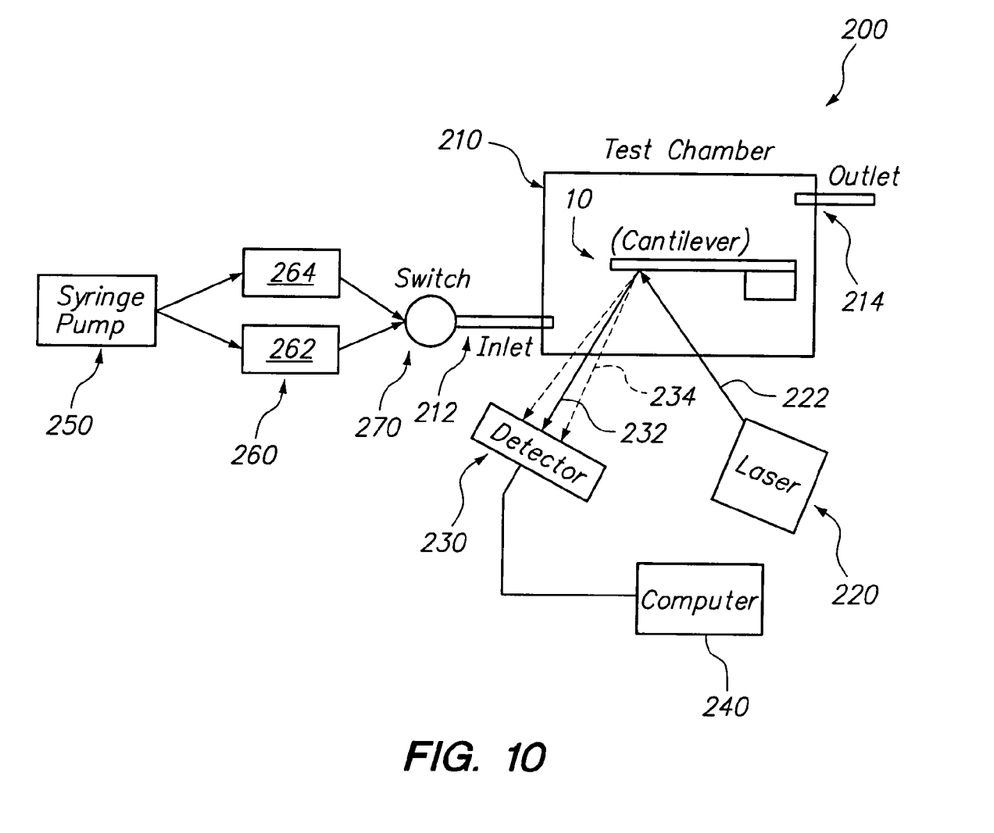
FIG. 10 is an optical detection system for measuring a deflection of a microcantilever beam upon detection of tobacco-specific nitrosamines (TSNAs).

FIG. 10 shows an optical detection system 200 for a deflection of a microcantilever beam 10 for the detection of tobacco-specific nitrosamines 110. As shown in FIG. 10, the optical system 200 can include a test chamber 210 having an inlet 212 and an outlet 214 to circulate the tobacco-specific nitrosamine medium, and having at least one microcantilever beam 10 contained therein. The optical system 200 also includes a laser 220, which is adapted to emit an incident beam 222 towards the microcantilever beam 10 and a photosensitive detector or detector 230 to receive the incident beam 222 upon reflection from the microcantilever beam 10. It can be appreciated that the change in position of the incident beam 222 is typically proportionate to the deflection and rotation of the microcantilever beam 10. For example, when the microcantilever beam 10 is not deflected, the incident beam 222 from laser 220 is reflected along a first path 232 toward the photosensitive detector or detector 230. However, after the microcantilever 10 has been deflected, the incident beam 212 will instead be reflected along a second path 234 toward the photosensitive detector or detector 230.

The system 200 also preferably includes at least one channel 260, which is adapted to contain test sample 262 either in liquid or gas phase and a cleaning agent 264, which are injected via a pump 250 to the test chamber 210. The system 200 can include a switch 270 for directing the test sample 262 or cleaning agent 264 to the chamber 210. As shown in FIG. 10, the microcantilever beam 10 is preferably functionalized to be chemically or physically active upon exposure to tobacco-specific nitrosamines (TSNAs) contained within the test sample 262. Upon exposure to tobacco-specific nitrosamines (TSNAs), the microcantilever beam 10 will undergo an induced stress at the interface of receptor layer 20 of the microcantilever beam 10 and the surrounding test sample 262, resulting in a deflection of the microcantilever beam 10. The deflection of the microcantilever beam 10 is then measured, wherein the deflection indicates a presence of tobacco-specific nitrosamines in the test sample 262.

In addition, a suitable computing apparatus or device 240 (e.g., a computer) having a suitable software program will preferably be used, wherein the software program is adapted to receive information from the detector 230 from each microcantilever beam 10. The software program will then preferably store the data, and then upon request displays the data or results in a desired format, including digital readings or printouts of instantaneous readings or quantitative readings over a specified period of time. It can be appreciated that based on the received information, the software program will be capable of positively identifying the presence of trace amounts of tobacco-specific nitrosamines 110 (TSNAs), or alternatively confirm the absence of trace amounts of tobacco-specific nitrosamines 110 (TSNAs) within the medium 50 (e.g., an assay or an analyte). It can be appreciated that the system 200 will also preferably includes a quantitative ability to provide a detection range for tobacco-specific nitrosamines (TSNAs) of 400 to 50,000 ppb (parts-per-billion), and more preferably a detection range of 1,000 to 5,000 ppb.

In use, a suitable handheld device will preferably be reusable, wherein the device can be cleaned using a cleaning agent 264 or other suitable cleansing or cleaning method. The system 200 can also include a syringe pump 250, at least one medium source 260 and a switch 270 attached to the inlet of test chamber 210.

The deflection of the microcantilever beam 10 can be measured with subnanometer sensitivity by using any suitable method including optical, piezo-resistive, capacitance, and piezo-electric detection methods.

In accordance with another embodiment, the system 200 can include a plurality of microcantilever beams 10 form a sensor array 160 with integrated piezo-resistor for measuring the deflection of the microcantilever beams 10. The piezo-resistor utilizes the electronic properties of the microcantilever to measure its bending, such that the laser 220 and the detector 230 can be removed. Highly doped silicon has the property to change its resistivity under mechanical strain. Accordingly, if such a doped layer is incorporated into the microcantilever beam 10, its bending can easily be measured by determination of the electrical resistance of the microcantilever beam 10. Typically, the piezo-resistors will contain a specific electronic material with high electrical resistivity, which converts the mechanical motion associated with the deflection or bending of the microcantilever beams 10 into an electrical signal. The deflection is read as a change in resistance of the integrated resistor using appropriate electronic circuits and converted to a piezo-resistive readout.

In accordance with another embodiment, the system 200 without the laser 220 and the detector 230 as shown in FIG. 10 can be incorporated into a handheld microcantilever-based sensor system to identify and monitor tobacco-specific nitrosamines 110 (TSNAs). The system 200 will preferably be comprised an array 160 of 4-16 piezo-resistive microcantilever beams 10 and an associated electronic readout system (not shown). The microcantilever beams 10 will preferably be functionalized with chemicals as indicated and shown in FIGS. 4-8, which have specific bonding and recognition with tobacco-specific nitrosamine (TSNA) molecules. It can be appreciated that tobacco-specific nitrosamine 110 (TSNA) detection can be accomplished by observing the resistance difference of microcantilever beams 10 before and after exposure to tobacco-specific nitrosamines (TSNAs).

Figure 11:
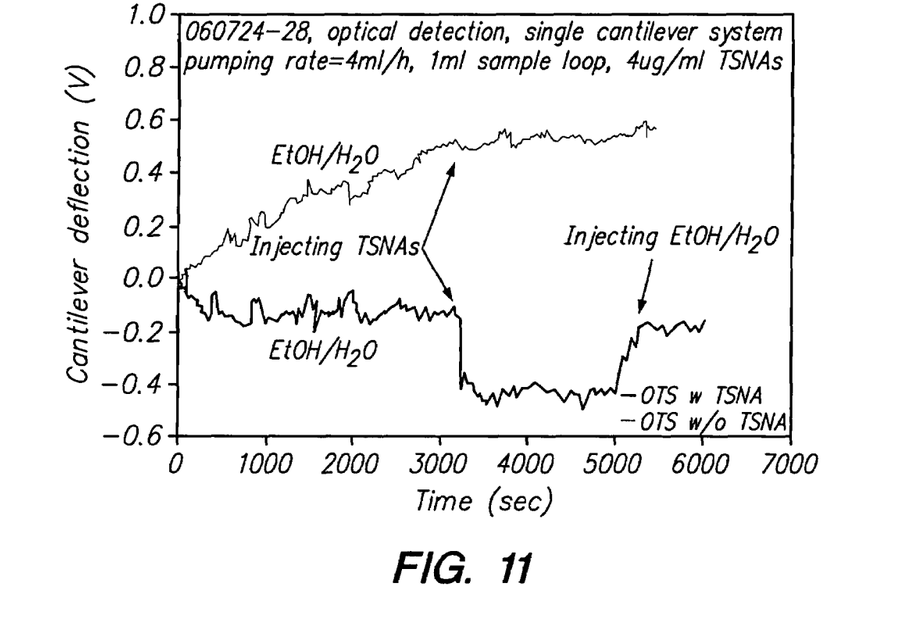
FIG. 11 is a graph of microcantilever deflection versus time in accordance with one embodiment.

FIG. 11 shows a graph of cantilever deflection versus time in accordance with one embodiment, wherein cantilevers are functionalized with self-assembled monolayers of octadecyl-trichlorosilane (OTS) with and without TSNAs molecules as templates, respectively. As shown in FIG. 11, the cantilever deflection versus time utilizing an optical detection system with a single microcantilever beam 10 with a pump rate of 4 ml/h, 1 ml sample loop and 4 µg/ml of TSNA was performed.

Figure 12:
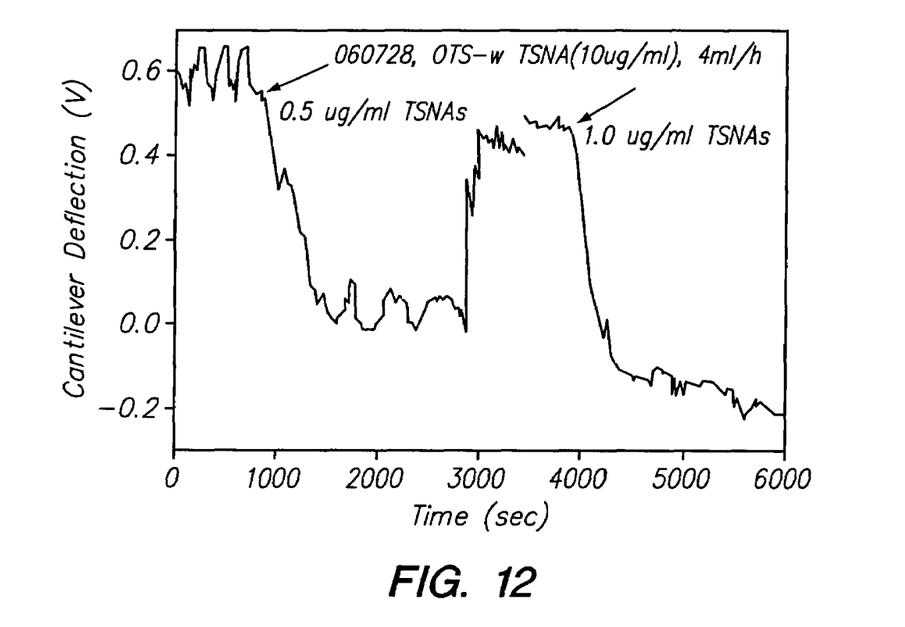
FIG. 12 is a graph of microcantilever deflection versus time for microcantilever deflection vs. tobacco-specific nitrosamines (TSNAs) concentration in accordance with one embodiment.

FIG. 12 shows a graph of cantilever deflection versus time for microcantilever deflection vs. TSNAs concentration in accordance with one embodiment, wherein cantilever is functionalized with a self-assembled monolayer of octadecyl-trichlorosilane (OTS) in presence of TSNAs as templates.

Figure 13A:
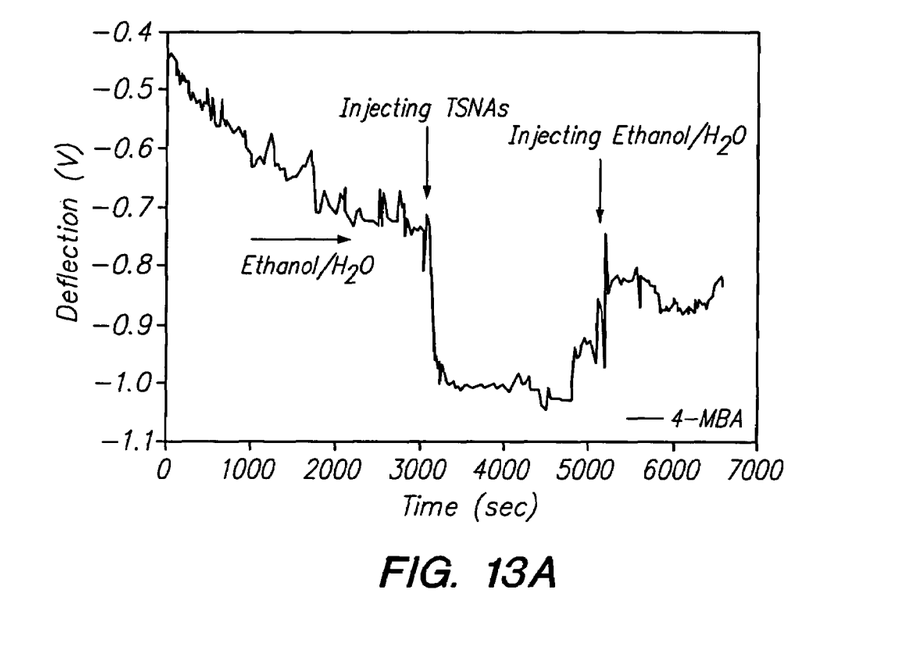
FIGS. 13A and B are graphs of microcantilever deflection versus time in accordance with a further embodiment.
Figure 13B:
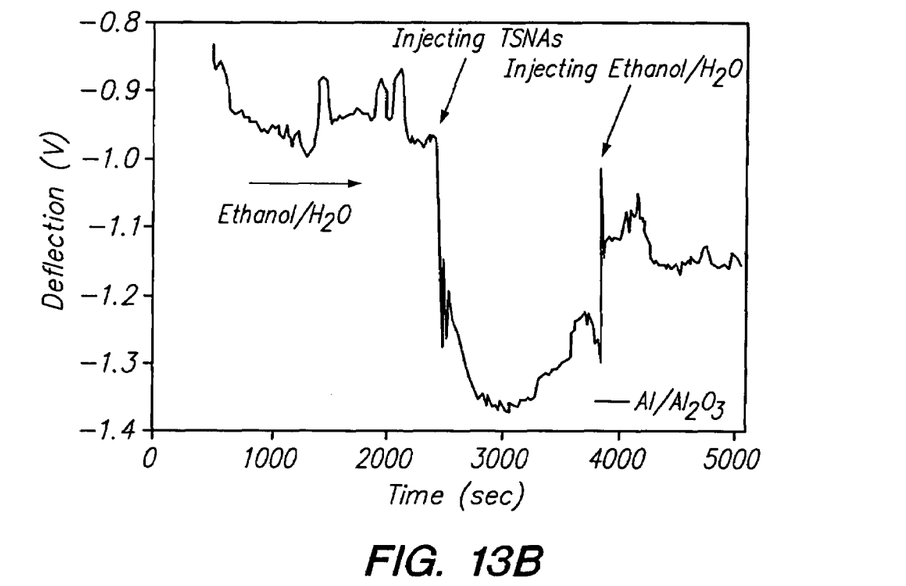

FIGS. 13A and B show graphs of cantilever deflection versus time in accordance with a further embodiment, wherein cantilever A is functionalized with a self-assembled monolayer of 4-mercaptobenzoic acid (4-MBA); cantilever B is modified by depositing 5 nm chromium (Cr) adhesive layer and 40 nm aluminum (Al) film.

It will be understood that the foregoing description is of the preferred embodiments, and is, therefore, merely representative of the article and methods of manufacturing the same. It can be appreciated that variations and modifications of the different embodiments in light of the above teachings will be readily apparent to those skilled in the art. Accordingly, the exemplary embodiments, as well as alternative embodiments, may be made without departing from the spirit and scope of the articles and methods as set forth in the attached claims.

What is claimed is:

1. A method of detecting tobacco-specific nitrosamines comprising:
    exposing at least one microcantilever beam to a medium, which may contain tobacco-specific nitrosamines, the at least one microcantilever beam having a silicon base layer and a receptor layer comprising a gold coating with a plurality of thiol molecules having a sulfur head and a carboxyl-terminated group on the gold coating; and
    measuring a deflection of the at least one microcantilever beam, and correlating the deflection to a presence of tobacco-specific nitrosamines in the medium.

2. The method of claim 1, wherein the thiol molecules form a self-assembled monolayer of thiol molecules with the carboxyl-terminated groups on the gold coating.

3. The method of claim 2, wherein the at least one microcantilever beam undergoes deflection due to the hydrogen bonding between the —COOH in the thiol self-assembled monolayer and the —N—N═O in the tobacco specific nitrosamines.

4. The method of claim 1, further comprising an integrated piezo-resistor, which converts the deflection of the at least one microcantilever beam into an electrical signal, and wherein the electrical signal is converted into an electronic readout.

5. The method of claim 1, wherein the medium is in either a liquid or a gas phase.

6. A method of detecting tobacco-specific nitrosamines comprising:
    exposing at least one microcantilever beam to a medium, which may contain tobacco-specific nitrosamines, the at least one microcantilever beam has having a silicon base layer and a receptor layer having a metal or metal oxide coating, and wherein the metal or metal coating is comprised of aluminum (Al), platinum (Pt), or palladium (Pd); and
    measuring a deflection of the at least one microcantilever beam, and correlating the deflection to a presence of tobacco-specific nitrosamines in the medium, wherein the at least one microcantilever beam undergoes deflection due to an interaction between the metal or metal oxide coating and basic pyrrolidine-N and pyridine-N of the tobacco-specific nitrosamines.

7. The method of claim 6, further comprising an integrated piezo-resistor, which converts the deflection of the at least one microcantilever beam into an electrical signal, and wherein the electrical signal is converted into an electronic readout.

8. The method of claim 6, wherein the medium is in either a liquid or a gas phase.

9. A method of claim 1, further detecting tobacco-specific nitrosamines comprising:
 exposing an array of microcantilever beams to a medium, which may contain tobacco-specific nitrosamines, and wherein the array of microcantilevers comprises:
  at least one microcantilever beam having a silicon base layer and a receptor layer comprising a gold coating with a plurality of thiol molecules having a sulfur head and a carboxyl-terminated group on the gold coating; and
  at least one microcantilever beam having a silicon base layer and a receptor layer comprising a metal or metal oxide coating; and
 measuring a deflection of the array of microcantilever beams, and correlating the deflection to a presence of tobacco-specific nitrosamines in the medium.

10. The method of claim 9, further comprising an integrated piezo-resistor, which converts the deflection of the at least one microcantilever beam into an electrical signal, and wherein the electrical signal is converted into an electronic readout.

11. The method of claim 9, wherein the thiol molecules form a self-assembled monolayer of thiol molecules with the carboxyl-terminated groups on the gold coating.

12. The method of claim 11, wherein the at least one microcantilever undergoes deflection due to the hydrogen bonding between the —COOH in the thiol self-assembled monolayer and the —N—N=O in the tobacco-specific nitrosamines.

13. The method of claim 9, wherein the medium is in either a liquid or a gas phase.

* * * * *